US00PP32023P2

(12) United States Plant Patent
Sal

(10) Patent No.: US PP32,023 P2
(45) Date of Patent: Jul. 28, 2020

(54) ***ALLIUM* PLANT NAMED 'SERENDIPITY'**

(50) Latin Name: ***Allium* hybrid (Linnaeus)**
Varietal Denomination: Serendipity

(71) Applicant: Eric M. Sal, Hamilton, MI (US)

(72) Inventor: Eric M. Sal, Hamilton, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/602,728

(22) Filed: Nov. 26, 2019

(51) Int. Cl.
*A01H 5/02* (2018.01)
*A01H 5/12* (2018.01)
*A01H 5/04* (2018.01)
*A01H 6/04* (2018.01)

(52) U.S. Cl.
USPC ..... Plt./263.1
CPC ..... *A01H 6/045* (2018.05)

(58) Field of Classification Search
USPC ..... Plt./263.1
CPC ..... A01H 5/02; A01H 5/04; A01H 5/12
See application file for complete search history.

*Primary Examiner* — Kent L Bell

(57) ABSTRACT

A new and distinct cultivar of ornamental onion, *Allium* plant named 'Serendipity', with compact, medium-sized habit, heavily-glaucous, upright, stiff, strap-like, blue-green foliage without twisting, and numerous, tightly-clustered, reddish-purple flowers forming in globose umbels over a long period beginning in late July.

1 Drawing Sheet

Botanical classification: *Allium* hybrid (Linnaeus).
Variety denomination: 'Serendipity'.

STATEMENT REGARDING PRIOR DISCLOSURES UNDER 37 CFR 1.77(B)(6)

The first public disclosure of the claimed plant, in the form of a photograph and brief description on a website operated by Walters Gardens, Inc. on Feb. 1, 2019. The claimed plant was first sold on Feb. 4, 2019 by Walters Gardens, Inc., who obtained the plant and all information relating thereto, from the inventor. No plants of *Allium* 'Serendipity' have been sold in this country or anywhere in the world, nor has any disclosure of the new plant been made, more than one year prior to the filing date of this application, and such sale or disclosure within one year was either derived directly or indirectly from the inventor.

BACKGROUND AND ORIGIN OF THE PLANT

The present invention relates to the new and distinct ornamental onion, *Allium* 'Serendipity' was discovered by the inventor at a wholesale perennial nursery in Zeeland, Mich., USA as non-induced, sport mutation from *Allium* 'Millenium' in Sep. 13, 2012. The new plant was divided from the mother plant the same time.

*Allium* 'Serendipity' has been successfully asexually propagated by garden bulb division method since 2014 at a wholesale perennial nursery in Zeeland, Mich. and found to be stable and produce identical plants that maintain the unique characteristics of the original plant through multiple generations.

SUMMARY OF THE PLANT

*Allium* 'Serendipity' differs from its sport parent as well as all other ornamental onion known to the applicant. The most similar known *Allium* cultivars are: 'Medusa' U.S. Plant Pat. No. 28,701, *Allium senescens* 'Blue Eddy' (not patented), *Allium tanguticum* 'Summer Beauty' (not patented), 'Lavender Bubbles' U.S. Plant Pat. No. 31,126, and 'Millenium' (not patented). 'Blue Eddy' has shorter and more twisted leaves, flowers and overall habit and smaller flower globes and lighter colored flowers. 'Summer Beauty' has less glaucous foliage, lighter flowers in larger umbels and produces no seed. 'Lavender Bubbles' is slightly shorter in habit, blooms later with darker purple flowers and has more twisted foliage. 'Millenium' has foliage that is less glaucous blue-green.

*Allium* 'Serendipity' differs from these above cultivars and all unregistered cultivars known to the inventor in that it has:

1. Heavily glaucous, upright, stiff, strap-like, flattened, blue-green foliage without twisting;
2. Compact habit, drought tolerant, and deer resistant, medium-sized clumps;
3. Numerous, tightly-clustered, reddish-purple flowers forming dense globose umbel;
4. Strong stems hold flowers heads upright through flowering and seed production.

BRIEF DESCRIPTION OF THE DRAWINGS

The photographs of the new plant demonstrate the overall appearance of the plant, including the unique traits. The colors are as accurate as reasonably possible with color reproductions. Ambient light spectrum, source and direction may cause the appearance of minor variation in color.

DETAILED BOTANICAL DESCRIPTION

Figure 1:
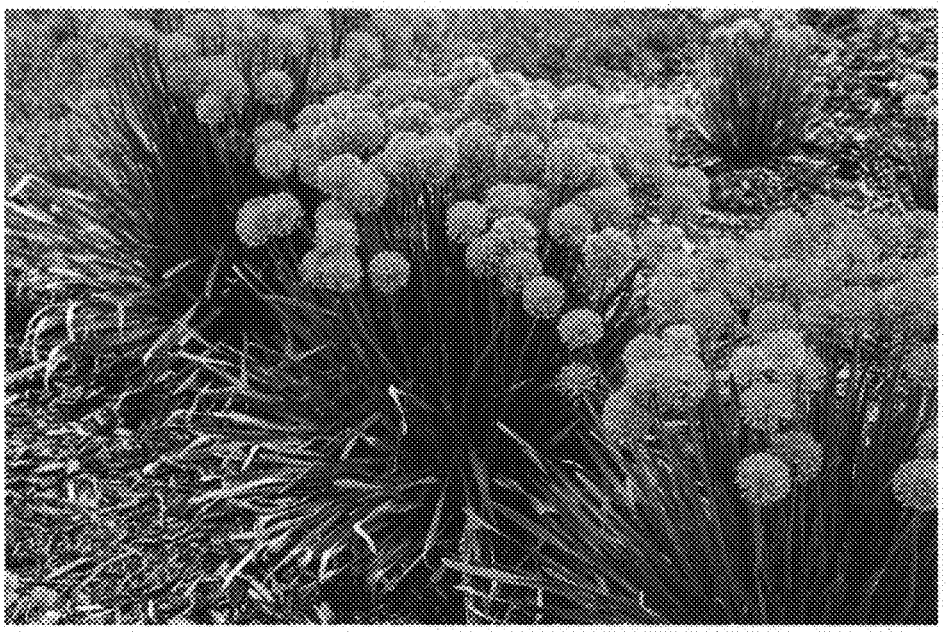
FIG. 1 shows the side-view habit of three-year-old plants in early flowering.
Figure 2:
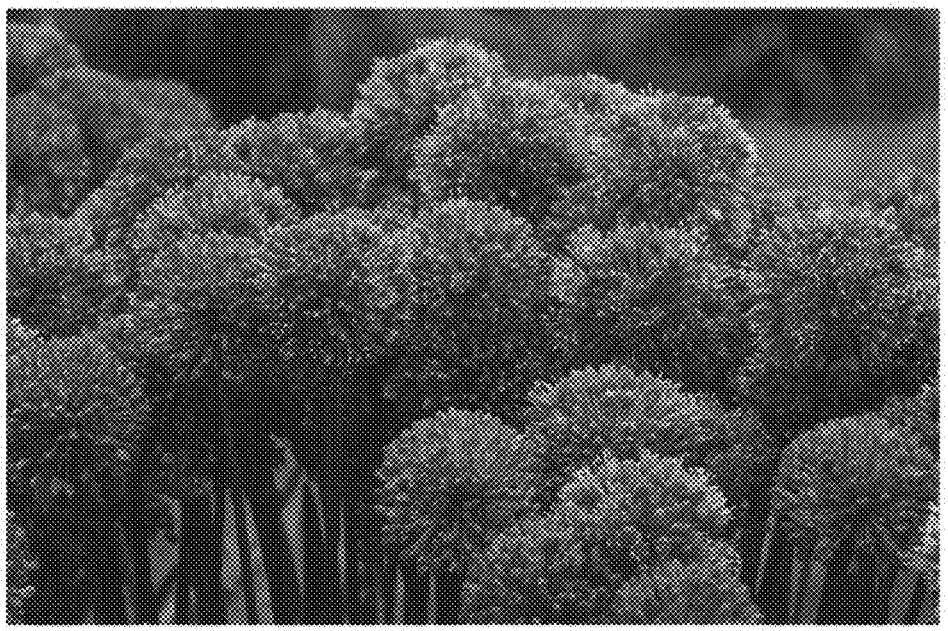
FIG. 2 shows a close-up of the umbels with flowers and buds.

The following descriptions and color references are based on the 2015 edition of The Royal Horticultural Society Colour Chart except where common dictionary terms are used. The new plant, *Allium* 'Serendipity', has not been observed under all possible environments. The phenotype may vary slightly with different environmental conditions, such as temperature, light, fertility, moisture and maturity levels, but without any change in the genotype. The following observations and size descriptions are of a three-year-old plant in a trial garden of a wholesale perennial nursery in Zeeland, Mich. under full sun with supplemental water and fertilizer as needed.

Botanical classification: *Allium* hybrid;

Parentage: Sport mutation of 'Millenium';

Propagation method: By garden bulb division;

Growth rate: Vigorous, flowering in 4 liter containers in about 12 weeks;

Rooting habit: Fibrous from base of bulbs, lightly branching; color nearest RHS 158C;

Plant habit description: Dense clump of bulbs with sessile rosulate foliage about 69.0 cm across and about 30.0 cm tall; flowering to about 47.0 cm tall;

Bulbs: Elongated conical shape; about 6.0 cm long and 1.4 cm diameter at base; about 60 per plant; color nearest RHS 155D;

Leaves: Sessile; linear; glaucous, glabrous, dull surfaces; semi-sarcous; simple, margin entire; acute apex, truncate clasping base; mostly flat; about 29.0 cm long and about 10.0 mm across at base; arranged in two-ranked tuffs from bulb; fragrance onion-scented;

Leaf color: Expanding leaves adaxial and abaxial base nearest RHS 145B, distally adaxial and abaxial nearest RHS 138B; mature leaves adaxial base nearest RHS NN155C and abaxial base nearest RHS 145B, distally adaxial and abaxial nearest RHS 137A;

Leaf venation: Parallel; color same as leaf abaxial and adaxial;

Inflorescence: Terminal umbel; round; with flowers facing in all directions; about 55 mm diameter; about 200 to 300 flowers per umbel; about 50 to 70 inflorescences per plant;

Flowering period: Beginning late July for about six weeks; individual umbels effective for about 20 days;

Blooming habit: With upright globe in bud, remaining upright as initial flowers open; one terminal umbel inflorescence per stem;

Buds one day prior to opening: Ellipsoidal; about 6.0 mm long and 4.0 mm diameter at base;

Bud color: Nearest RHS 76B in proximal 4 mm with apex nearest RHS 77A;

Flowers: Campanulate; incomplete; perfect; with two sets of three tepals, outer set smaller than inner; inferior ovary; actinomorphic; upward and outwardly facing depending on position in umbel; individually effective about four to six days;

Flower size: From base to exerted stamens to about 10.0 mm long and about 7.0 mm across;

Tepals (outer set): Lanceolate to deltoid; concavo-convex; glabrous; lustrous; acute apex, fused truncate base; about 5.0 mm long and about 2.0 m across;

Tepal (inner set): Ovate to deltoid; flat; glabrous; lustrous; acute apex, broadly acute base; about 6.5 mm long and about 2.0 mm across;

Tepal color (outer set): Adaxial base nearest RHS 76D, apex nearest RHS N75C; abaxial longitudinal center nearest RHS N75C and margins nearest RHS 76C;

Tepal color (inner set): Adaxial longitudinal center nearest RHS N75C, margin nearest RHS 76C; abaxial margins nearest RHS 76C and longitudinal center nearest RHS N75C;

Pedicel: Cylindrical; stiff, upward and outwardly facing depending on orientation in umbel; glabrous; glaucous; about 16.0 mm long and about 0.7 mm diameter;

Pedicel color: Nearest a blend between RHS 146B and RHS 138A;

Peduncle: Glabrous, glaucous; slightly applanate, flattened trapezoid in cross-section; about 42.0 cm long, base about 4.0 mm wide and about 3.0 mm thick;

Peduncle color: Base nearest RHS 138A;

Gynoecium: Pistil single; to about 9.0 mm long;

*Style*.—Single, cylindrical, glabrous, to about to 6.0 mm long and about 0.4 mm across when mature; color nearest a blend between RHS 76A and RHS 76B.

*Stigma*.—Globose; about 0.2 mm across; color lighter than RHS 76D.

*Ovary*.—Distinctly tri-loculed; obcordate; about 3.0 mm long and 3.0 mm across at rounded apex and truncate base; color nearest blend between RHS N78D and RHS 75B.

Androecium: Six; exserted to about 9.0 mm long;

*Anther*.—Oblong ellipsoidal; about 2.0 mm long and about 0.7 mm wide; basifixed; longitudinal; color nearest RHS 165C.

*Filament*.—Exserted; glabrous; cylindrical; about 7.0 mm long and 0.3 mm at base; color nearest RHS 83D.

*Pollen*.—Abundant; color nearest RHS 158D.

Receptacle: Turbinate; about 1.5 mm tall and 2.0 mm across top, tapering to pedicel; color nearest RHS 138A;

Fruit: Tri-valved loculicidal capsule; about 6.0 mm long and 4.5 mm across; typically dehiscing to within about 1.0 mm of base; one to three seeded; color upon maturity nearest RHS 199D;

Seed: Elliptic, flattened along one long side; about 2.5 mm long and about 1.5 mm across; color nearest RHS 202A;

Disease and pest resistance: Ornamental onions typically resist deer feeding. Resistance beyond that of other ornamental onion has not been observed. *Allium* 'Serendipity' plants grow best with good drainage and are able to tolerate some drought when established. Hardiness at least from USDA zone 4 through 8.

I claim:

1. A new and distinct cultivar of ornamental onion, plant named *Allium* 'Serendipity', as herein described and illustrated.

* * * * *